United States Patent [19]
Olson et al.

[11] Patent Number: 4,883,064
[45] Date of Patent: Nov. 28, 1989

[54] METHOD AND SYSTEM FOR GATHERING ELECTROCARDIOGRAPHIC DATA

[75] Inventors: Richard J. Olson, Ramsey; David C. Gust, Andover, both of Minn.

[73] Assignee: EquiMed Corporation, Plymouth, Minn.

[21] Appl. No.: 122,796

[22] Filed: Nov. 19, 1987

[51] Int. Cl.$^4$ ............................................. A61B 5/04
[52] U.S. Cl. ................................... 128/696; 128/904
[58] Field of Search .............. 128/695, 696, 699, 700, 128/702, 704, 706, 904; 364/413.06

[56] References Cited

U.S. PATENT DOCUMENTS

| | | | |
|---|---|---|---|
| 3,426,150 | 2/1969 | Tygart | 128/696 |
| 3,895,316 | 7/1975 | Fein | 128/696 |
| 4,565,201 | 1/1986 | Lass | 128/696 |
| 4,593,702 | 6/1986 | Kepski et al. | 128/696 |

OTHER PUBLICATIONS

"Three Channel Electrocardiographs", Chart Published in Immediate Care Center News, 1987.
Brochure: Mac 12, Marquette Electronics, Inc., 1985.
Brochure: MacPC, Marquette Electronics, Inc., 1985.
Brochure 398 E310, Burdick Corp.
Advertisement: Omnigraph 4000, Telemed Division, Hays Medical, Inc., 1986.
"Holter Monitors—Comparison of Product Specifications", Chart Published in Immediate Care Center News, May 1987.
Brochure: Zymed Holter System.
Brochure: CardioMemo (showing transmitter only on front page), Instromedix, Inc., 1984.
Brochure: CardioMemo (showing transmitter and receiver on front page), Instromedix, Inc., 1984.
Brochure: Instant Replay, Instromedix, Inc., 1984.
Brochure: CarryAll, Instromedix, Inc. 1986.
Brochure: Teletrace, Medtronic, Inc.
Brochure: Retrospective ECG Memory Loop Recorder, Cardiac Evaluation Center, Inc.

*Primary Examiner*—Francis J. Jaworski
*Assistant Examiner*—George Manuel
*Attorney, Agent, or Firm*—Dorsey & Whitney

[57] ABSTRACT

A method of gathering electrocardiographic data is disclosed wherein the EKG data is collected by sequentially monitoring the difference in electrical potential measured at each of at least three patient leads for a time period greater than 15 seconds, preferably for equal time periods of 20 seconds each. Although more than three leads and longer monitoring time periods may be used, a 60-second three-lead EKG data sample in accordance with the present invention is clinically sufficient to monitor cardiac function and to diagnose most cardiac dysfunctions.

A system for collecting such electrocardiographic data is also disclosed. The system allows the collected data to be stored for later translation and interpretation. The stored data may also be communicated over phone lines for translation and interpretation at a remote site by trained individuals.

28 Claims, 12 Drawing Sheets

METHOD AND SYSTEM FOR GATHERING ELECTROCARDIOGRAPHIC DATA

FIELD OF THE INVENTION

This invention relates to sensing of the condition and activity of the heart by measuring electrocardiographic data. In particular, this invention relates to a new and improved method of gathering electrocardiographic data and to a system for collecting such data and transmitting the collected data to a remote location for analysis.

BACKGROUND OF THE INVENTION

Since the time it was discovered that the pumping heart was central to maintaining life, medical science has developed new and improved ways to monitor cardiac function and to diagnose cardiac dysfunction. Currently, the electrocardiograph or "EKG" (alternatively, "ECG") is considered the best method for monitoring cardiac function.

The electrocardiograph instrument monitors cardiac function by recording changes in electrical potential detected by electrodes attached at various locations on the monitored patient's skin. The electrodes measure fluctuations in electric potential caused by depolarization and repolarization of the cardiac muscle during each heartbeat. The EKG instrument translates the fluctuations in electric potential at various locations into a set of traces on an electronic screen or paper "rhythm strip" chart, producing the familiar spiked beat pattern. The magnitude and timing of various fluctuations as represented by a trace or rhythm strip are then analyzed to provide information relating to heart rate, coordination between the various chambers of the heart, condition of the heart tissue and cardiac dysfunction.

An individual trace or rhythm strip is a representation of data collected from one electrode "lead". A "lead" is a combination of two electrodes which produces an electropotential "picture" of the heart from a given angle. Though electrodes can be placed at many different locations on a patient's skin, the placement of electrodes at ten specific locations on the patient's skin have been set by convention. The ten standard electrode locations produce a total of twelve different "conventional leads."

Many EKG instruments monitor all twelve conventional leads, providing very detailed and comprehensive data concerning cardiac function. Some instruments can selectively monitor and record a collection of three, four or six leads selected by the user. Other instruments monitor all twelve leads simultaneously and display three, four, six or twelve traces at a time and incorporate the ability to display different lead configurations during an EKG examination. All of these systems produce traces on a monitor or a rhythm strip as the data is collected.

Unfortunately, obtaining a complete conventional twelve-lead diagnosis requires (1) an instrument which is usually both expensive and, as a result of its size, difficult to transport easily; (2) the presence of a physician or EKG technician at the site where the data is collected; and (3) an examination which is invasive for the patient since the patient must be disrobed above the waist and, in some cases, shaved so that certain of the electrodes can be attached to the chest. While monitoring a subset of the twelve lead system alone may provide sufficient data to recognize many features of cardiac function and dysfunction, one-lead and two-lead systems may not allow a physician or EKG technician to differentiate particular arrythmic conduction disturbances or ischemic events.

In many situations, including home-based post-operative care, patient screening and outpatient surgical procedures, it is desirable to monitor cardiac activity and to detect irregularities therein without making the complete diagnosis provided by a conventional twelve lead EKG instrument. For example, during many dental and oral surgery procedures the patient is exposed to extreme physiological stress which can result in cardiac dysfunction or arrest. By monitoring the patient's cardiac function before treatment, during treatment and/or when signs of extreme stress (heavy breathing, accelerated pulse) are observed the quality of patient care is increased and a cardiac event may be averted.

Although non-cardiology professionals, including dentists and outpatient surgeons, are interested in monitoring the heart function of their patients before, during and after stressful procedures, they seldom use EKG technology because of the sizeable cost of EKG instruments and because of their lack of expertise in reading EKG data. Consultation with a cardiologist or EKG technician is usually necessary to translate the EKG data into information useful to the treating professional. Few non-cardiology professionals have such resources readily available and, as a result, the effects of stressful procedures upon patient cardiac function are often not monitored. Even when non-cardiology professionals have sought the counsel of cardiologists, e.g., in extreme emergency situations during a procedure, the cardiologist is greatly hindered by the inability to examine any EKG data. Unless the cardiologist is present with the patient, it is often impossible to make a useful determination of the patient's condition without an EKG trace.

It would, therefore, be desirable to provide a simple, economical and non-invasive method and system to collect a clinically significant sample of electrocardiographic data. Preferably, such data should be collected in a manner such that it can be easily communicated to a cardiologist or EKG technician for interpretation.

SUMMARY OF THE INVENTION

In accordance with the present invention, a method of gathering electrocardiographic data is disclosed wherein the EKG data is collected by sequentially monitoring the difference in electrical potential measured at each of at least three patient leads for a time period greater than 15 seconds, preferably for equal time periods of 20 seconds each. Although more than three leads and longer monitoring time periods may be used, a 60-second three-lead EKG data sample is, as set forth below, clinically sufficient to monitor cardiac function and to diagnose most cardiac dysfunctions.

A system for collecting such electrocardiographic data is also disclosed. The system allows the collected data to be stored for later translation and interpretation. The stored data may also be communicated over phone lines for translation and interpretation at a remote site by trained individuals.

DETAILED DESCRIPTION OF THE INVENTION

The preferred embodiment of the method of the present invention generates a sample of patient EKG data comprising three equal segments of data from each of three pairs of electrodes attached to the patient's body, each data segment being about 20 seconds long.

To monitor cardiac function using the conventional lead system, electrodes are placed on each wrist, each ankle and at six locations on the chest. Each pair of electrodes or "lead" measures depolarization and repolarization of the cardiac muscle along a different plane by measuring the fluctuation in electrical potential between the two electrodes. In effect, the twelve conventional leads allow twelve potentiometric "pictures" to be taken of the heart from twelve different directions, thus providing the physician or EKG technician with a more detailed description of cardiac function. The twelve conventional leads are usually divided into three groups of leads: the Standard Limb Leads, the aVR-/aVL/aVF group and the V1-V6 group. The aVR-/aVL/aVF group forms leads from electrodes attached to the arms and legs. The V1-V6 group forms leads by pairing electrodes placed on the chest with an electrode on the patient's back, which acts as an "effective" negative electrode. Information regarding the various lead systems and their relation to cardiac function and EKG output can be found, for example, in Dubin, D., "Rapid Interpretation of EKG's," 3d ed. (COVER Publishing, Tampa, Fla. 1981).

Figure 3:
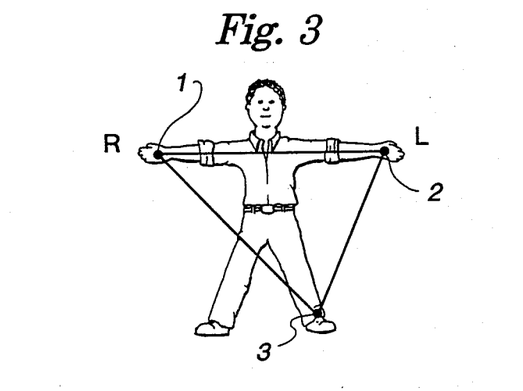
FIG. 3 is a schematic representation of Einthoven's triangle and the location of the electrodes forming the Standard Limb Leads.
Figure 4:
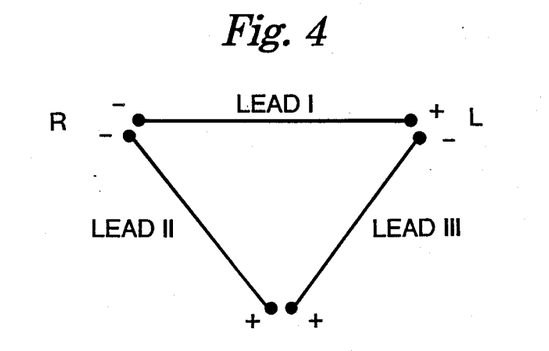
FIG. 4 is a schematic representation of the orientation and polarity of the Standard Limb Leads.

The Standard Limb Lead system can be traced to the original electrocardiographic lead system devised by Willem Einthoven (1860–1927). In his lead system the vector representing the direction and magnitude of the wave of cardiac depolarization was located in the center of a triangle formed by the left and right shoulders and the groin ("Einthoven's triangle"). For convenience the electrodes 1, 2 and 3 in the Standard Limb Lead system are connected to the right and left forearms or wrists and the left leg, each of which is considered an extension of the right shoulder, left shoulder and groin, respectively, as shown in FIG. 3. By convention, the Standard Limb Leads are connected to an EKG apparatus such that "Lead I" records the potential difference between the right arm and the left arm, with the left arm electrode being positive. "Lead II" records the potential difference between the right arm and the left leg, with the left leg electrode being positive. "Lead III" records the potential difference between the left arm and the left leg, with the left leg electrode being positive. FIG. 4 summarizes the orientation and polarity of the Standard Limb Leads.

Figure 5:
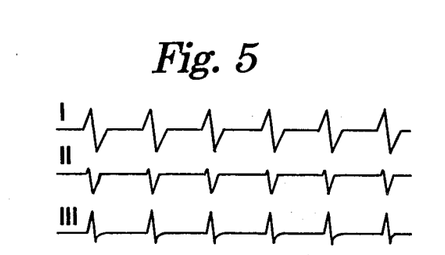
FIG. 5 is a representation of typical EKG traces from each of the Standard Limb Leads as they would appear on a typical EKG instrument.
Figure 6:
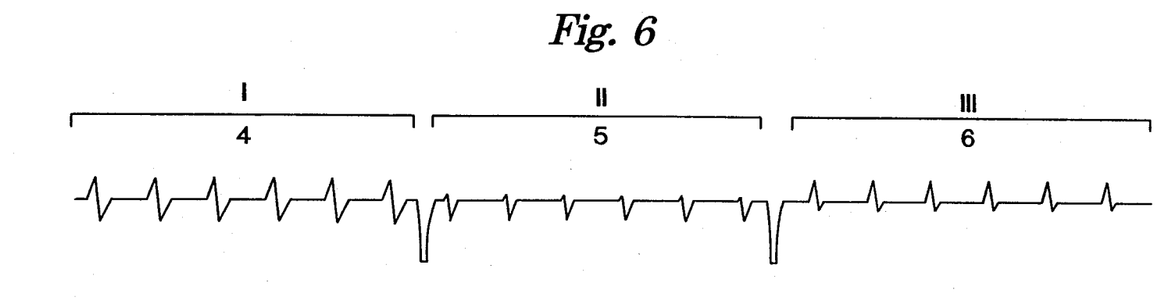
FIG. 6 is a representation of the same EKG trace from each of the Standard Limb Leads as collected by the method and system of the present invention.
Figure 7:
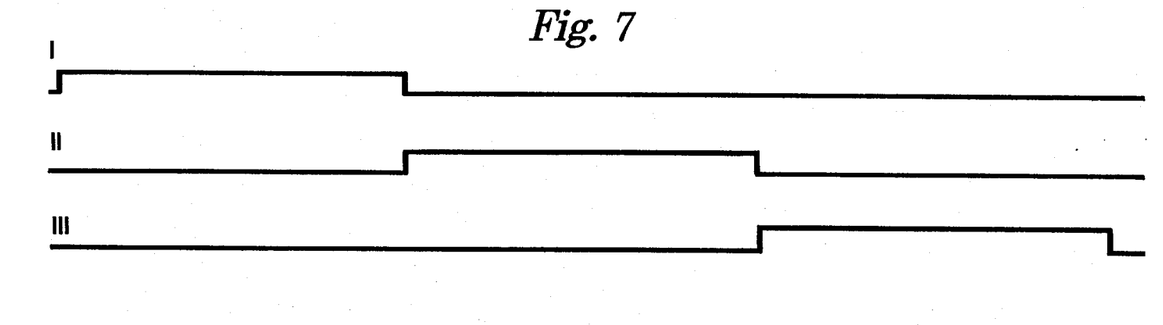
FIG. 7 is a switching diagram showing the pattern of switching between the Standard Limb Leads, in the device employed in the preferred embodiment of the present invention, in relation to the EKG trace depicted in FIG. 6.

In the preferred embodiment of the method of the present invention cardiac function is monitored using the Standard Limb Leads as shown in FIG. 3. In contrast to conventional measurements made using the Standard Limb Leads, the method of the present invention monitors cardiac function in a unique manner such that data is collected by measuring potential difference at Lead I for 20 seconds, then measuring potential difference at Lead II for 20 seconds, and finally measuring potential difference at Lead III for 20 seconds. FIGS. 5 and 6 depict two different forms of traces produced by monitoring these leads. FIG. 5 shows approximately 60 seconds of EKG data from an EKG instrument that read 20 seconds of data from all three leads simultaneously, with each lead displayed in parallel. FIG. 6 shows a trace or "rhythm strip" of the same cardiac activity depicted in FIG. 5 that was produced by the method of the present invention. A 20 second sample from a trace from Lead I 4 is followed by 20 seconds of trace from Lead II 5, and finally by 20 seconds of trace from Lead III 6.

Collecting 60 seconds of EKG data generated by three leads is normally adequate to adequately detect most cardiac rhythm anomalies, as most irregular rhythms will manifest themselves within the one-minute minimum monitoring period. A collection of data substantially less than one minute long may not represent enough EKG data to show even frequent arrythmias. The method of generating EKG data from three different leads for a total of 60 seconds normally provides sufficient data to detect rate and most rate anomalies (including ectopic pacemakers, sinus tachycardia, and sinus bradycardia), rhythm and most rhythm anomalies (including arrythymia, wandering pacemakers, fibrillations, premature beats, escape beats, arrest, heart blocks, paroxysmal tachycardia and flutter), axis and most axial anomalies, hypertrophy and infarctions. A three-lead system can also eliminate many instances of "invisible" symptoms found in systems using fewer leads. One-lead and two-lead monitoring are usually inadequate to differentiate particular arrythmic conduction disturbances or ischemic events that may not be visible on certain leads. For example, right bundle branch block can be seen on Lead II, but is not visible on Leads I and III. Three-lead monitoring also decreases the likelihood that the data will be useless because of artificial signals ("artifacts") in the trace, which are usually only seen in one (but not more than two) leads.

The preferred method of the present invention allows cardiac function to be monitored by three different leads over the course of a minimum required period of 60 seconds without requiring simultaneous monitoring or storing of signals from multiple leads. The method produces a smaller volume of data, which can be processed and analyzed more efficiently and economically without losing diagnostic certainty. Arrythmias or irregular beats show up during the tripartite monitoring period regardless of the lead being monitored. Irregularities in individual beats or beat patterns are detected by showing data from all three leads. Moreover, the decrease in the volume of data necessary to produce a clinically relevant analysis makes it easier to communicate the collected data to trained professionals for interpretation. The method of the present invention also requires less electronic memory to hold the resulting collection of EKG data. To produce a rhythm strip like that of the present invention a conventional twelve-lead EKG instrument would have to store twelve minutes of data (i.e., one minute from each lead). The present invention is more efficient in that it only requires storage of one minute of data (i.e., 20 seconds from each lead).

In alternative embodiments of the present invention, each lead could be monitored for more or less than 20 seconds. Although 10 seconds seems to be a minimum for obtaining a useful sample of data, some conditions may not manifest themselves in 30 seconds of trace. Monitoring periods longer than 20 seconds may, therefore, be used, but they negate in part the economic and efficiency advantages of collecting the necessary data in one minute.

Leads other than the Standard Limb Leads may also be used in the method of the present invention. The aVR/aVL/aVF lead group would be most appropriate. The V1 through V6 leads could also be used, although the method would then become more invasive in that the patient would have to be exposed above the waist, and shaved in some cases, for connection of the electrodes. Use of the Standard Limb Leads or the aVR/aVL/aVF lead group makes the method non-invasive since the electrodes can be conveniently attached to the patient's wrists and ankles.

Figure 1:
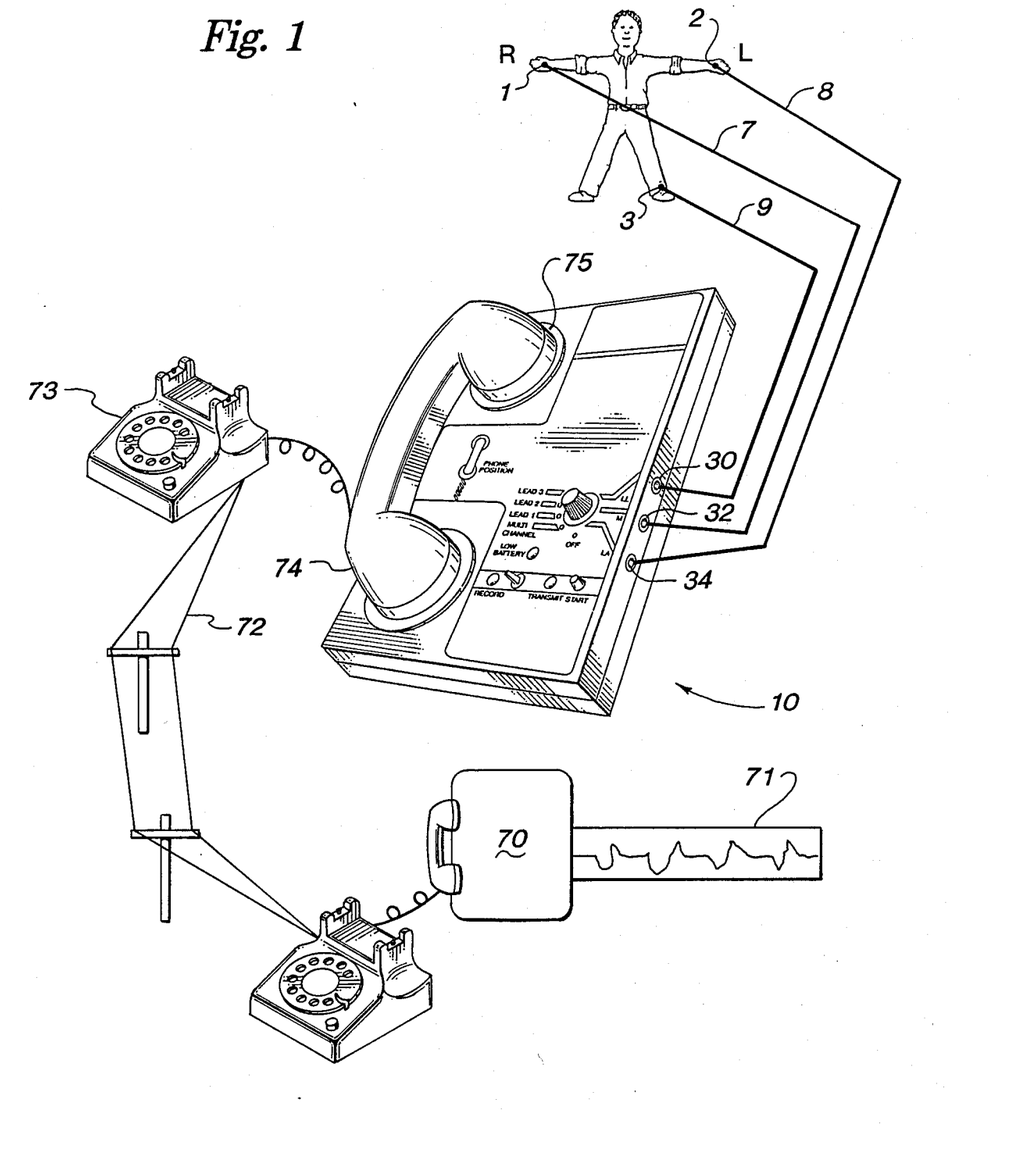
FIG. 1 is a schematic representation of the use of the method and system of the present invention.
Figure 2:
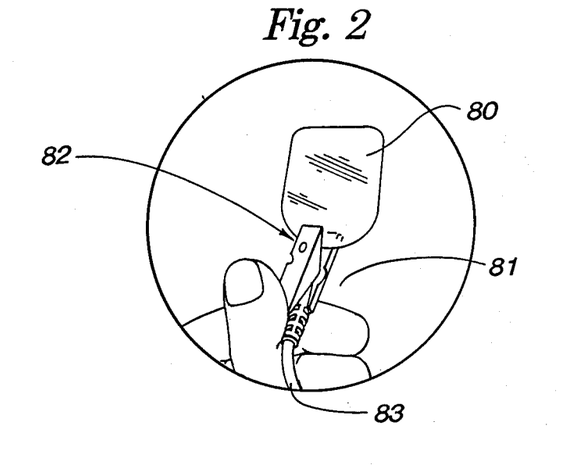
FIG. 2 is a pictorial representation of a conventional EKG electrode as used in the present invention.

In the preferred embodiment of a system for collecting EKG data according to the above-described method, standard EKG electrodes 1, 2 and 3 (commercially available from Andovar Medical, Haverhill, Mass.) are adhered to the palm side of each wrist and the inside of the left leg of the patient as shown in FIGS. 1, 2 and 3. Each electrode is comprised of an adhesive conductive tab 80 which is adhered to the patient's skin 81 and connected to a shielded cable 83 by a clip 82 (FIG. 2). The electrodes are connected to the apparatus 10 as shown in FIG. 1.

As shown in FIG. 1, when the collected electrocardiographic data is transmitted from apparatus 10 via telephone lines 72 to a remote receiver 70, the method and system of the present invention produce a paper chart or "rhythm strip" 71. The preferred embodiment of the rhythm strip, shown in FIG. 6, comprises a single 60-second trace which is made up of three sequential serial 20-second traces from Lead I, Lead II and Lead III, respectively. Alternative embodiments of the rhythm strip will vary in overall duration of the single trace and the duration of each sequential serial trace from each lead.

The apparatus of the present invention will next be described in detail. Referring to FIGS. 8 through 11, an apparatus 10 for monitoring, recording and transmitting EKG data in accordance with the present invention broadly includes an input buffer 12, switching network 14, comparator 16, A/D convertor 18, storage means 20, D/A convertor 22 and transmitter circuit 24. Standard electrodes 1, 2 and 3 are attached to the patient at various locations as previously described. The various operating modes of apparatus 10 are controlled by switches 26, 27 and 28. The EKG data collected by apparatus 10 may be transmitted over a standard telephone line 72 to a receiver 70 for analysis at a remote location or may be displayed locally on an EKG strip chart printer (not shown). A single-channel receiver in common use for accepting pacemaker data (e.g., Teletrace ® Telephone EKG Receiver, Model 9410, commercially available from Medtronic, Inc., Minneapolis, Minn.). Other currently-available single-channel receivers, which are for the most part used to receive data transmissions from pacemaker monitoring devices, may also be used. By having the apparatus 10 send to a widely-used type of receiver, persons using the method and system of the instant invention can send data to almost any cardiology office with nothing more than the apparatus 10 and a telephone 73. This arrangement makes the method and system both convenient and economical, because the advice of a cardiology professional can be sought without using additional or expensive EKG or receiving instrumentation and by only requiring the attention of the cardiologist when data is periodically transmitted and received.

Figure 8:
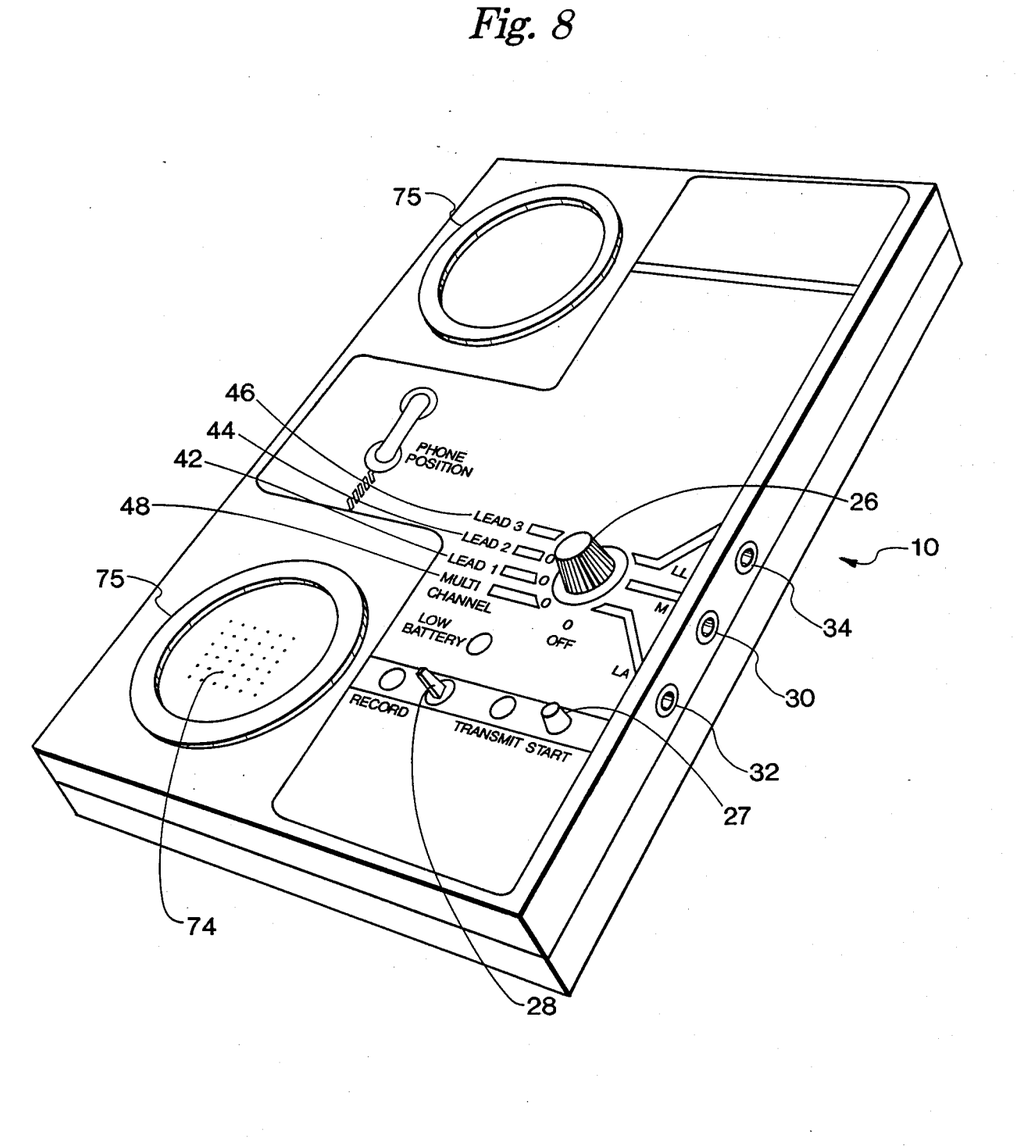
FIG. 8 is a pictorial view of the preferred embodiment of the system of the present invention.
Figure 9:
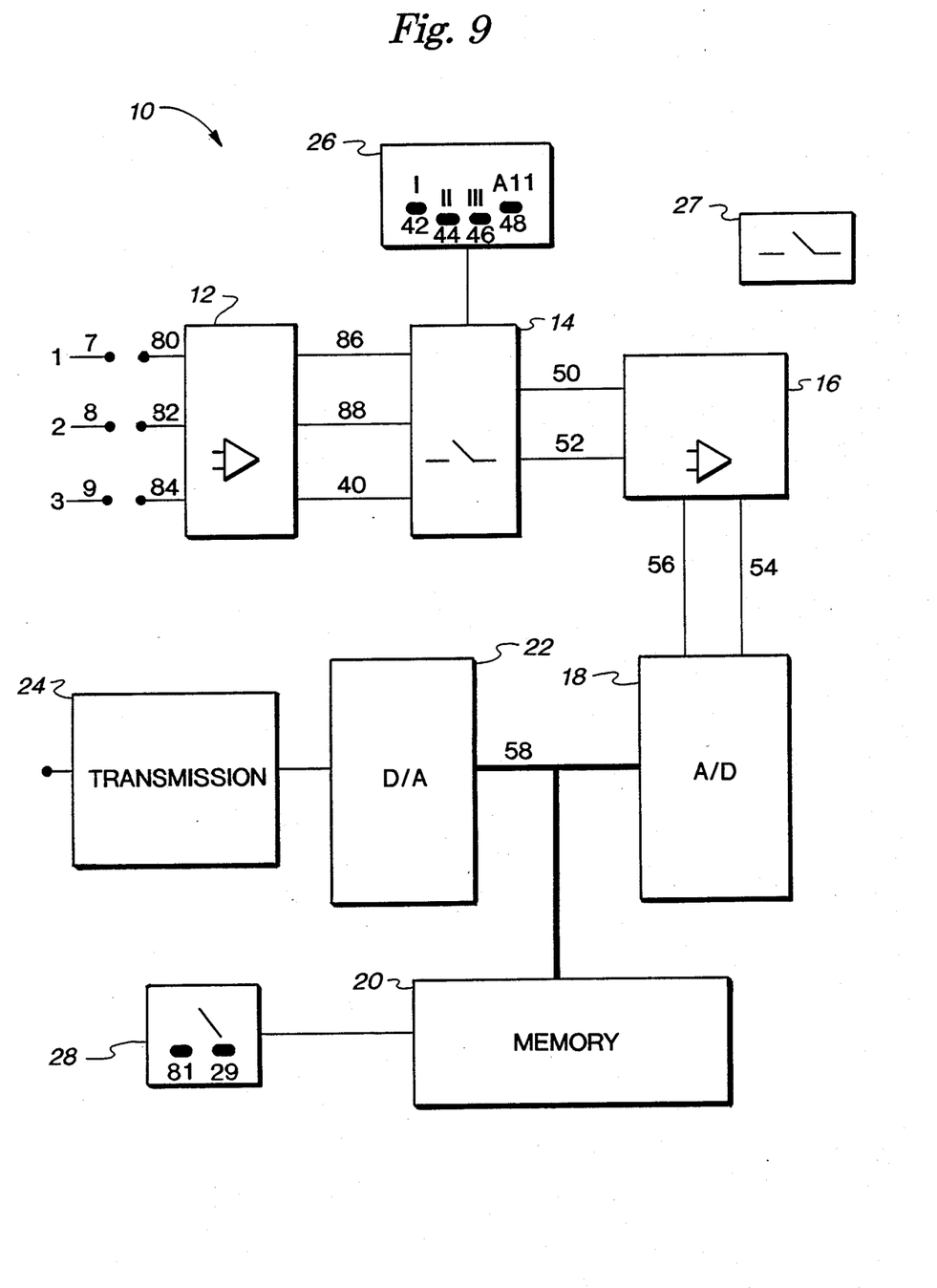
FIG. 9 is a block diagram of the EKG apparatus in accordance with the preferred embodiment of the present invention.

Referring now to FIGS. 8 and 9, the functional operation of apparatus 10 in accordance with the present invention will be described. Three electrodes 1, 2 and 3 are attached to the patient as previously described. Each of the electrodes 1, 2 and 3 are connected through shielded cables 7, 8 and 9 to input terminals 30, 32 and 34, respectively. Input buffer 12 receives and amplifies the analog input signals present on electrodes 1, 2 and 3. Once amplified, analog signals 36, 38 and 40, corresponding to the output of input terminals 30, 32 and 34, respectively, are presented to switching network 14 for selecting the desired pair of signals to be sensed.

For the Standard Limb Lead configuration, electrode 1 is attached to the patient's right arm; electrode 2 is attached to the patient's left arm; and electrode 3 is attached to the patient's left leg as previously described. For convenience and to insure that correct reading is obtained, each electrode and its corresponding input terminal are color-coded (electrode 1 and input terminal 30—white; electrode 2 and input terminal 32—black; and electrode 3 and input terminal 34—red). Switch 26 may be selectively positioned at any one of the four positions 42, 44, 46 and 48 to read continuously from Lead I, Lead II, Lead III or to automatically read sequentially from all three leads.

Apparatus 10 may be set to continuously present Lead I, Lead II or Lead III voltage to comparator 16 by setting switch 26 at positions 42, 44 or 46, respectively. As explained earlier, each lead must represent a pair of electrodes; Lead I ($V_2 - V_1$), Lead II ($V_3 - V_1$), Lead III ($V_3 - V_2$). By setting switch 26 to position 42, switching network 14 will continuously present analog signal 30 (electrode 1) at negative input 52 and analog signal 32 (electrode 2) at positive input 50, thus reading Lead I. With switch 26 at position 44, switching network 14 will continuously present analog signal 30 (electrode 1) at negative input 52 and analog signal 34 (electrode 3) at positive input 50, thus reading Lead II. With switch 26 at position 46, switching network 14 will continuously present analog signal 32 (electrode 2) at negative input 52 and analog signal 34 (electrode 3) at positive input 50, thus reading Lead III. It will be clear to those skilled in the art that any combination of input signals can be presented together on positive signal 50 and negative signal 52 by changing the position of electrodes 1, 2 and 3 on the patient's body, or by changing the order in which electrodes 1, 2 and 3 are connected to input terminals 30, 32 and 34.

Apparatus 10 also be set to sequentially monitor Leads I, II and III in accordance with the method of the present invention described previously. When switch 26 is in position 48, an internal timing circuit 145 (FIG. 10) is enabled which controls the length of time each lead is monitored and also controls sequencing through each lead. The pre-selected time interval is controlled by the clock frequency selected from clock 145 and is enabled by switch 27. When the time interval is completed, switching network 14 changes the combination of analog signals presented together at positive input 50 and negative input 52 to the next combination. Timing circuit 146 is also connected to start switch 27 to disable the storage and/or transmission of the EKG data after completion of one sequential cycle of the three leads. For the reasons set forth above, it is preferred that the pre-selected time interval be at least 20 seconds. To standardize interpretation of EKG data being transmitted, the time interval is normally set at 20 seconds by choosing biasing components for clock 145 such that a frequency of 100 Hz is presented to timing circuit 146.

Comparator 16 receives the particular combination presented at positive input 50 and negative input 52 and feeds A/D convertor 18 a reference voltage signal 54 (1.5 volts) and analog data signal 56 for conversion. A/D convertor 18 performs an 8 bit wide conversion on analog signal 56, sampling the signal at a sampling frequency of 250 Hz. Eight bit wide data bus 58 is connected to the output of A/D convertor 18 and to the input of D/A convertor 22. Data bus 58 is also connected to memory 20. By setting switch 28 at position 29 (Record), memory 20 is enabled to receive digital data from A/D convertor 18 via data bus 58 to be sequentially stored. When switch 28 is set at position 31 (Transmit), memory 20 retrieves the stored data and transfers it via data bus 58 to D/A convertor 22. When (i) switch 28 is set at position 31 (Transmit), (ii) switch 26 is in position 42, 44 or 46, and (iii) switch 27 is not enabled, the apparatus will continuously transmit data from the set of electrodes corresponding to the set position of switch 26.

Transmission circuit 24 receives the reconverted analog signal 60 from D/A convertor 22 which represents the particular combination of analog data signals as compared to the 1.5 volt reference voltage signal by comparator 16. Reconverted analog signal 60 is placed on a carrier frequency and converted into an audio signal 62 which is output through speaker 74. A typical acoustical coupler 75 receives the handset of telephone 73, thereby allowing the audio signal 62 to be sent out over the telephone lines 72 for remote analysis. In an alternative embodiment, audio signal 62 is received by a local EKG strip chart printer to allow the EKG data to be viewed locally.

Figure 10:
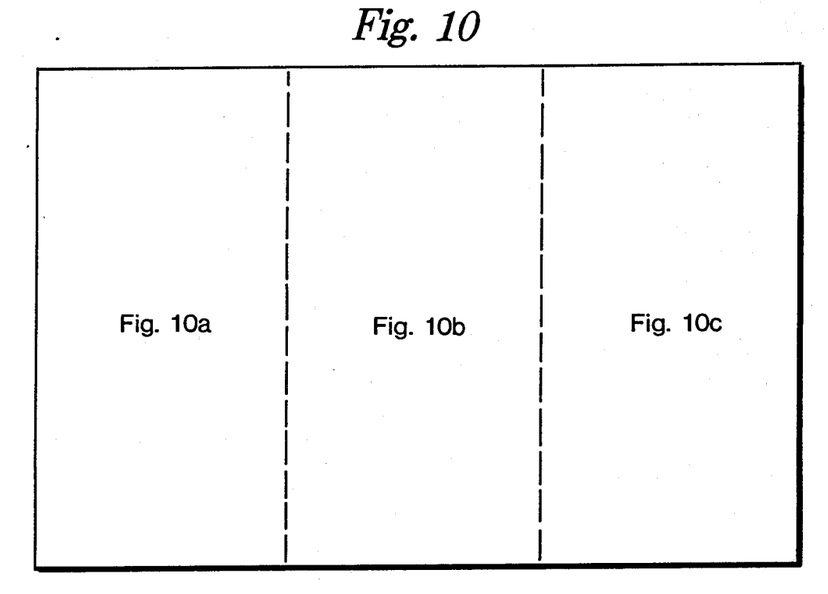
FIGS. 10, 10a-c and 11, 11a-c are electrical schematics of the preferred embodiment of the present invention as summarized in FIG. 9.
Figure 10A:
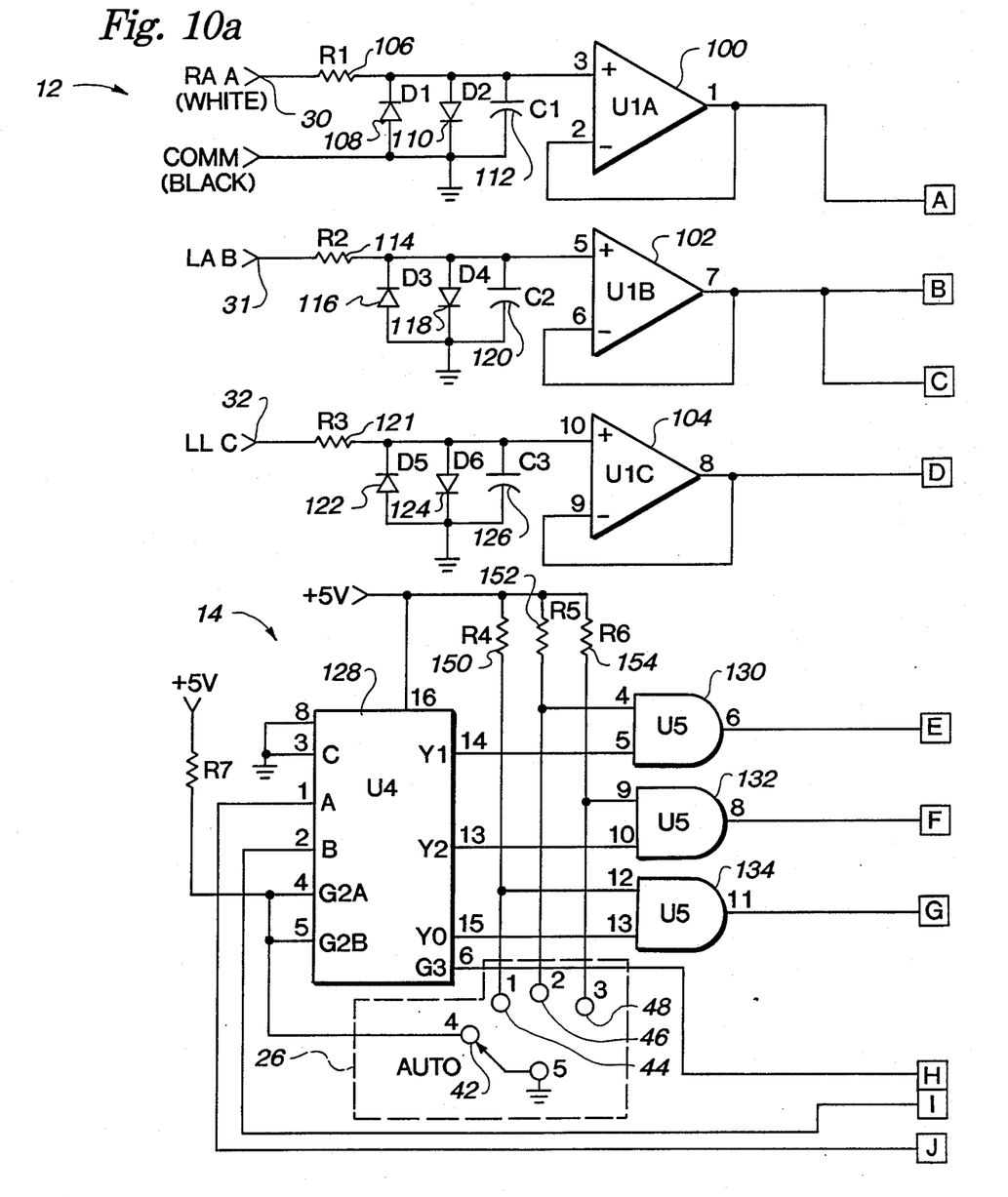
Figure 10B:
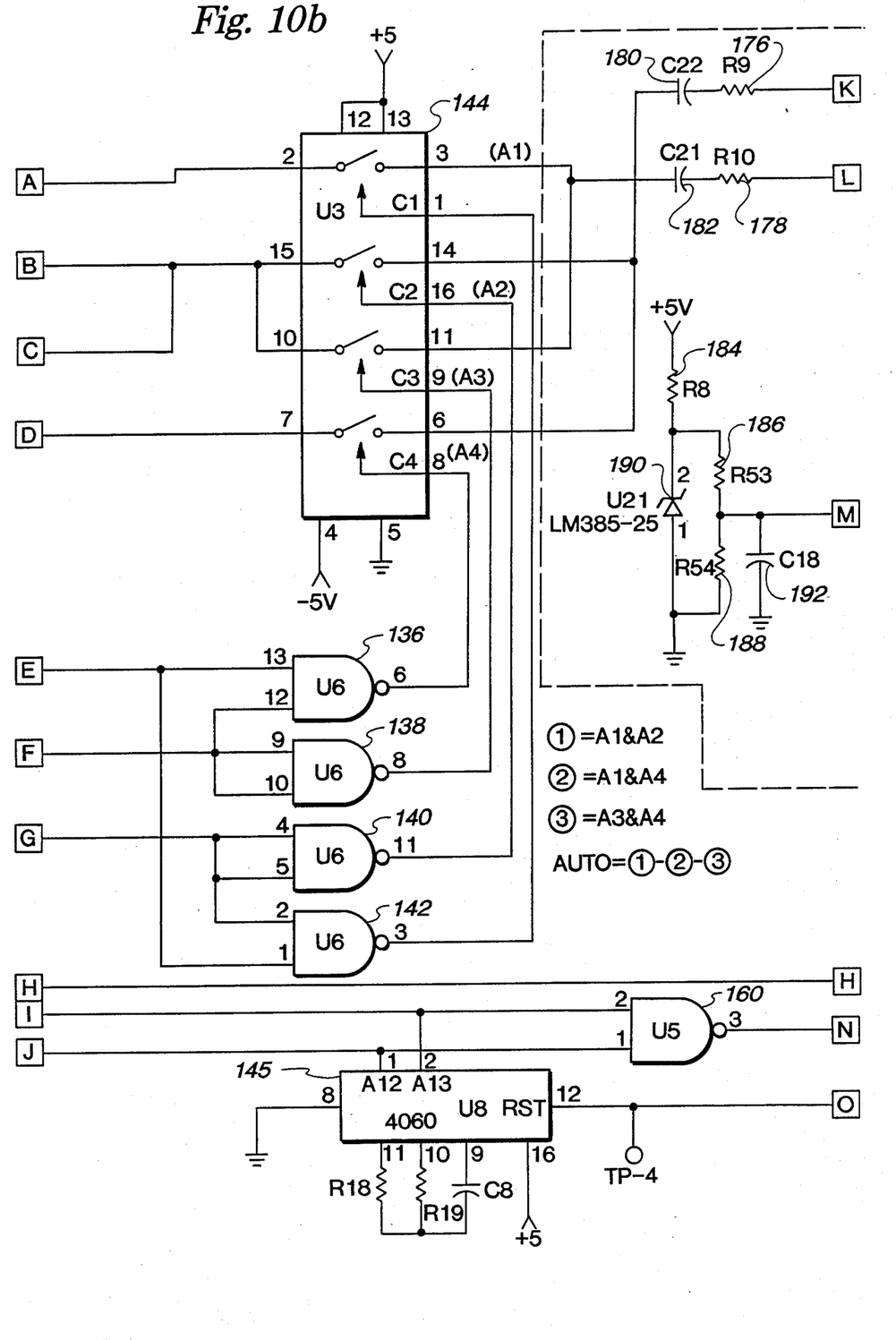
Figure 10C:
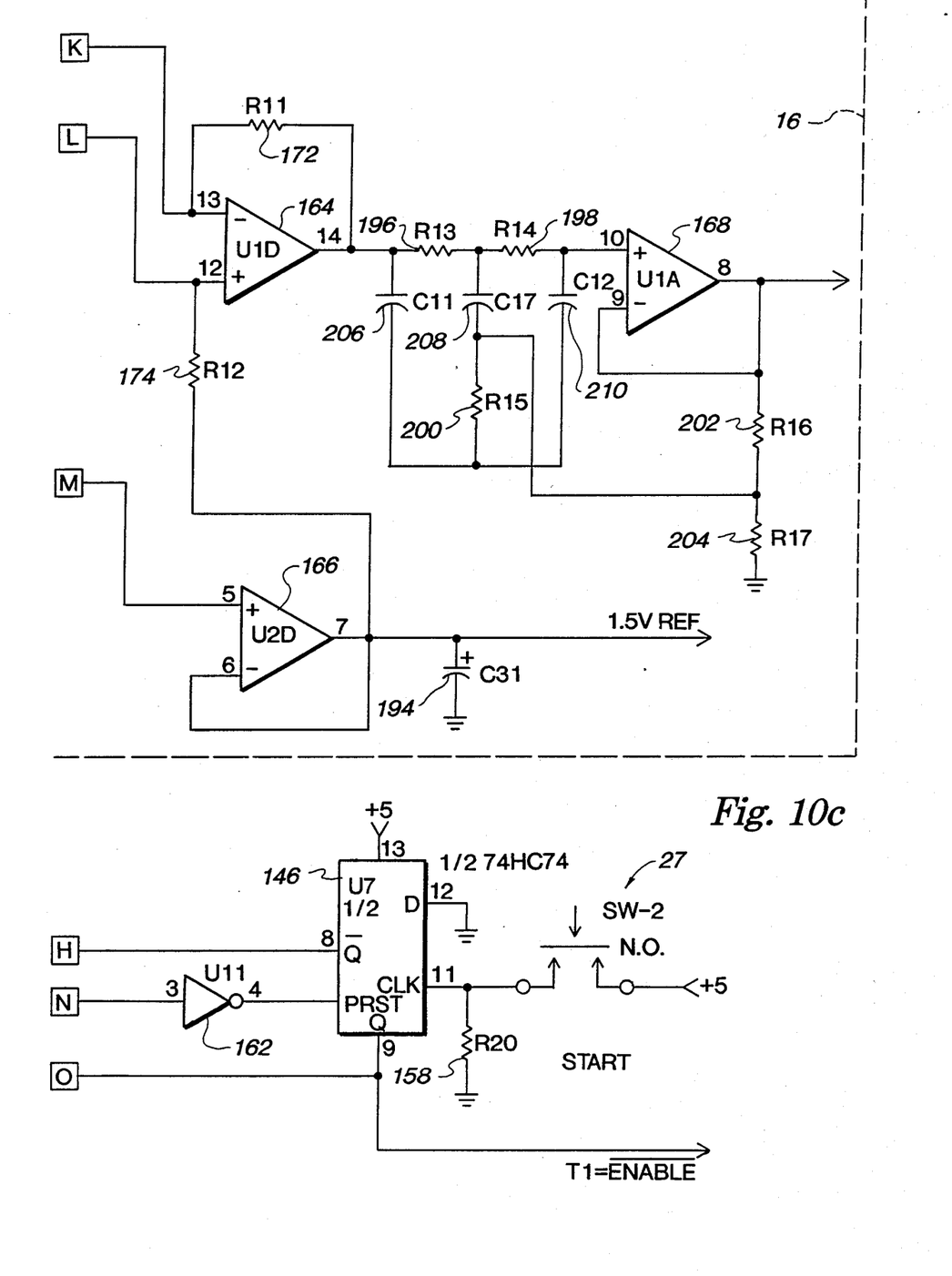
Figure 11:
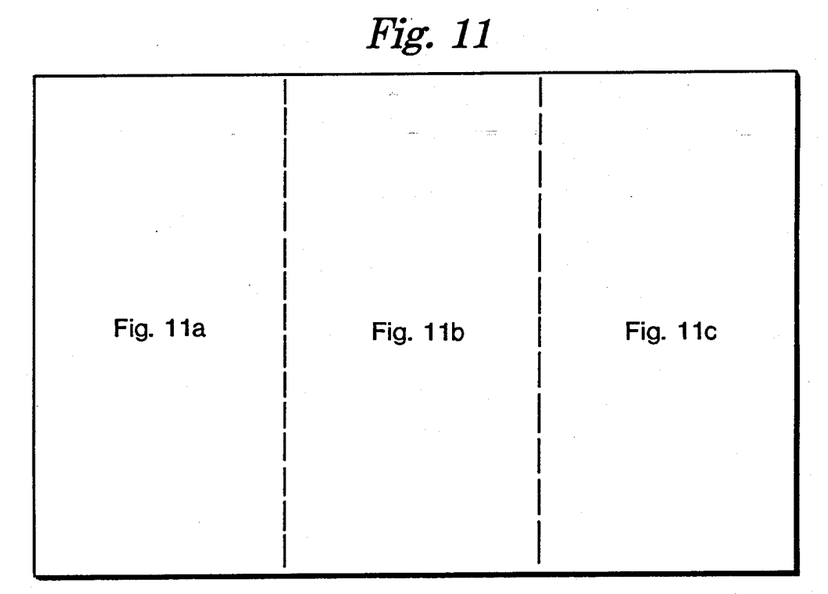
Figure 11A:
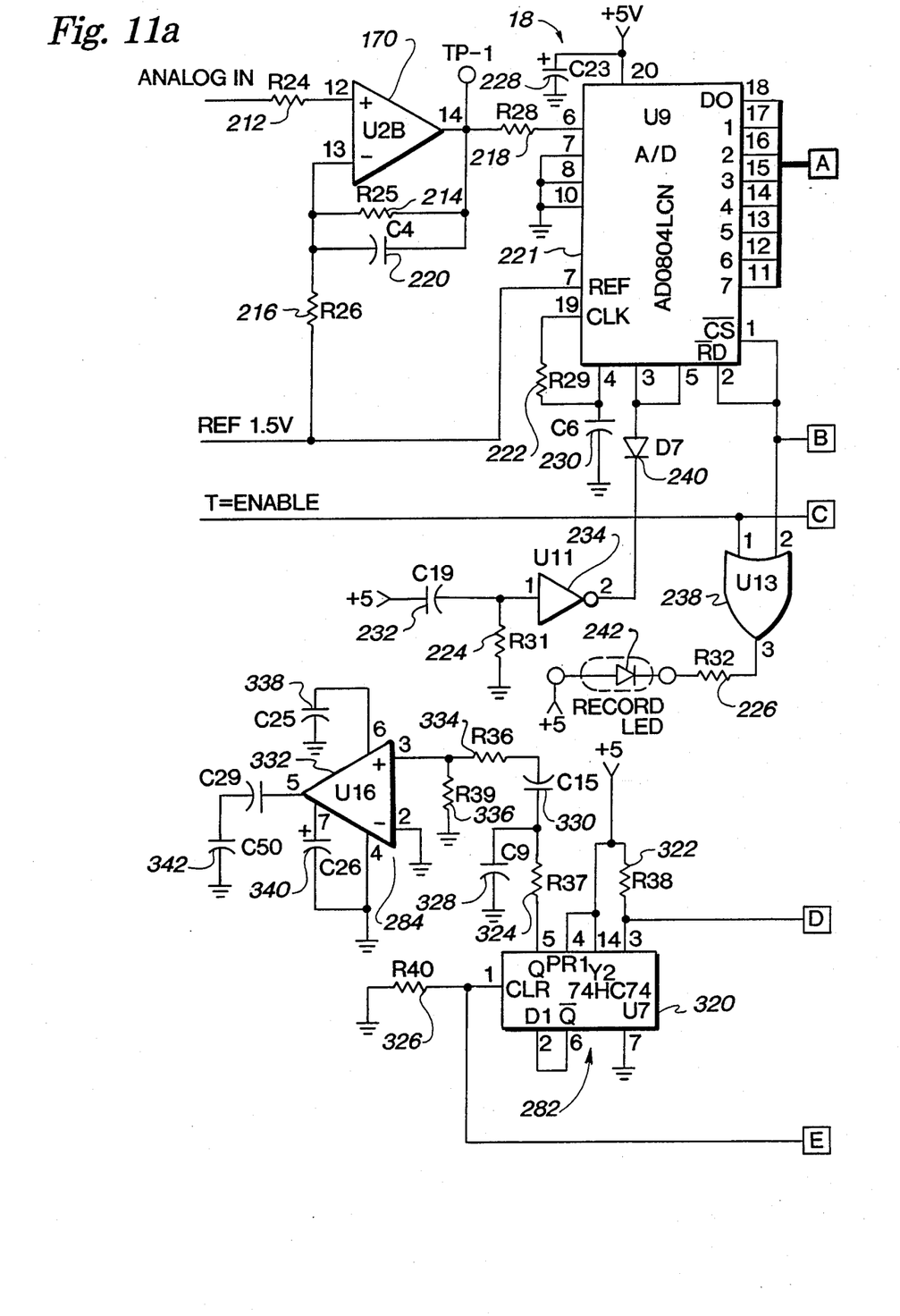
Figure 11B:
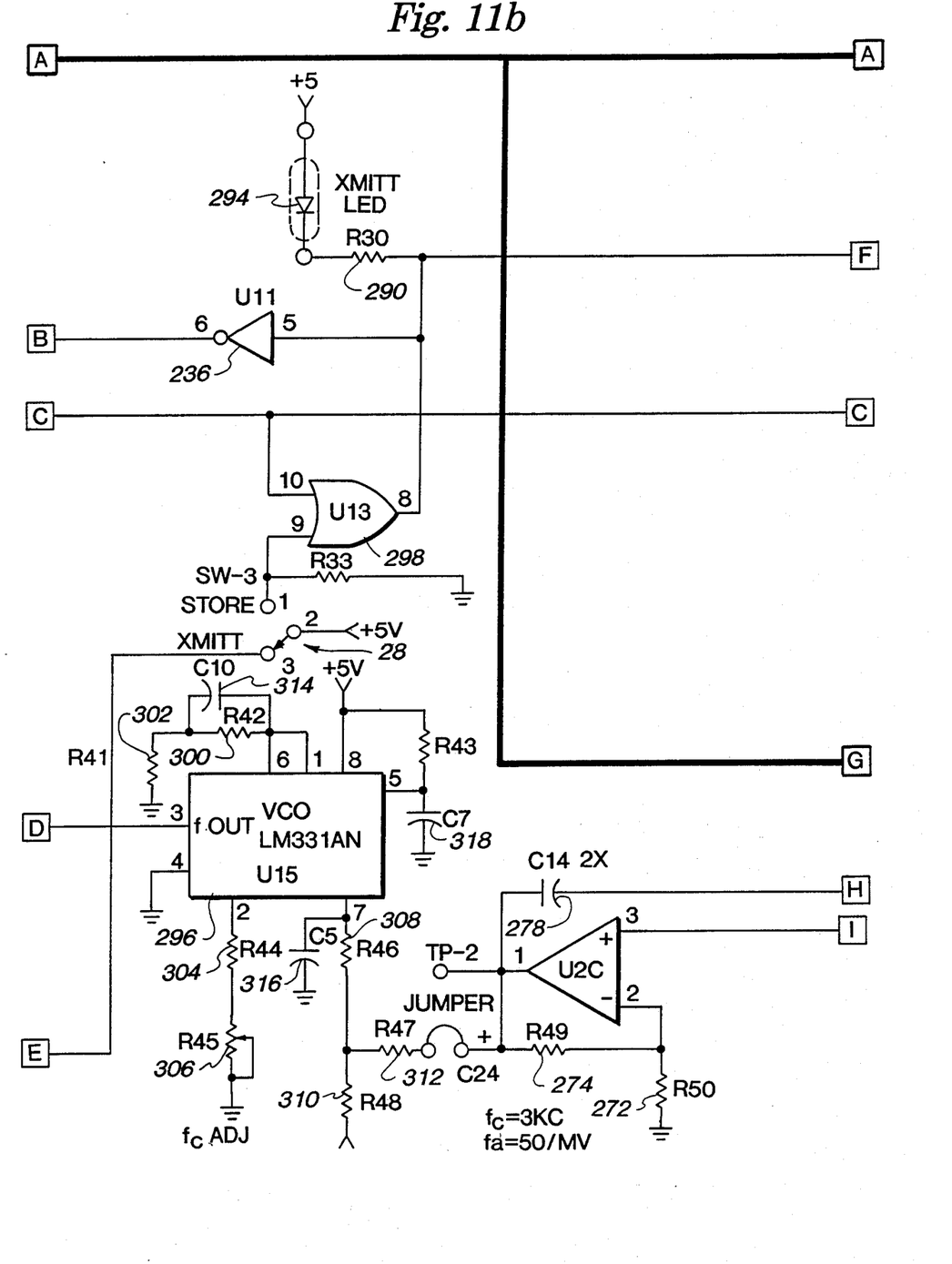
Figure 11C:
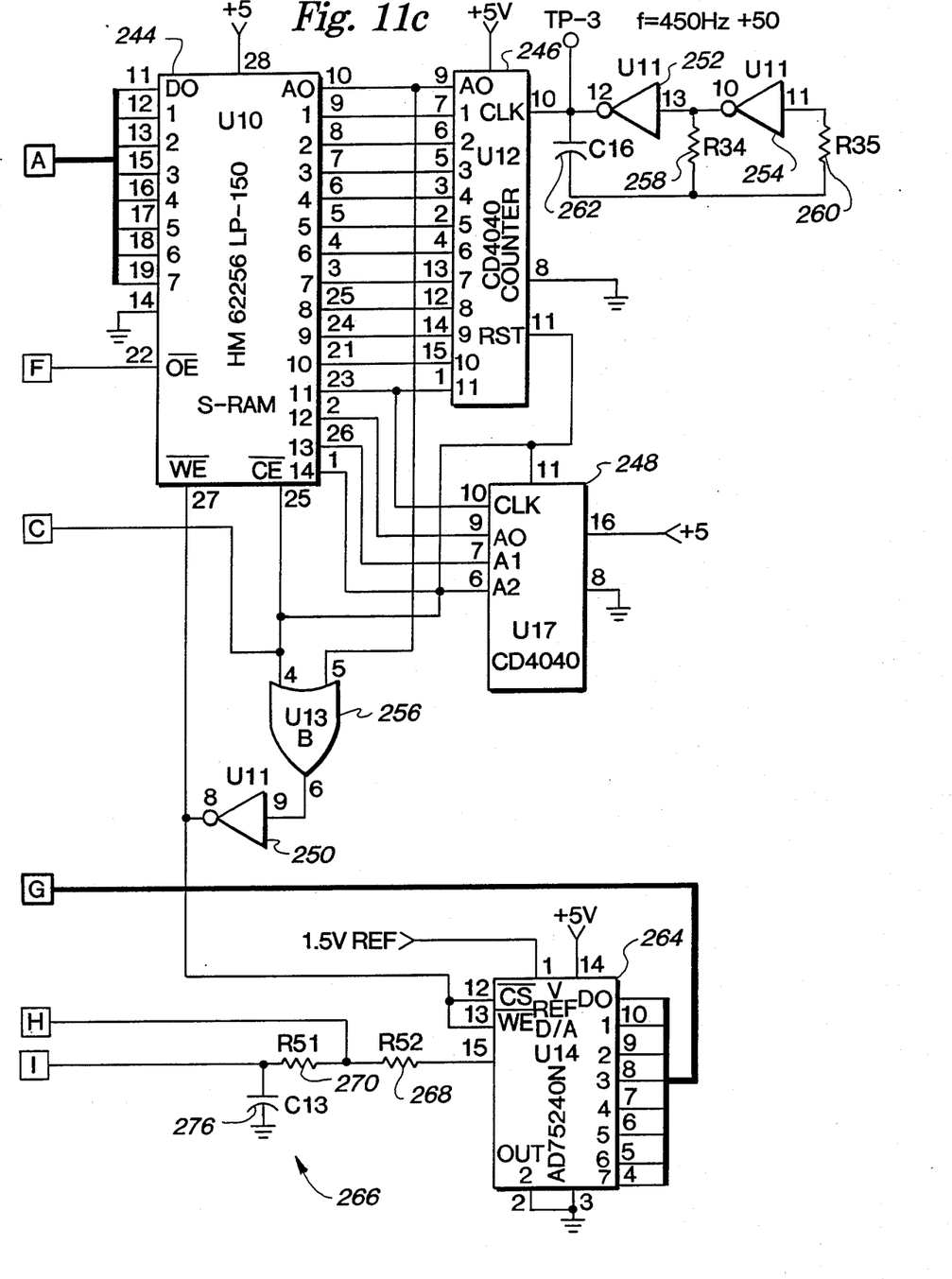

Referring to FIGS. 10 and 11, the circuitry of apparatus 10 in accordance with the preferred embodiment of the present invention is described in detail below.

Input buffer 12 comprises three operational amplifiers 100, 102 and 104 of a quad operational amplifier TL064ACN semiconductor chip (commercially available from Texas Instruments). Input terminal 30 connects to operational amplifier 100 through resistor 106, diodes 108 and 110 and capacitor 112. Input terminal 31 connects to operational amplifier 102 through resistor 114, diodes 116 and 118 and capacitor 120. Input terminal 32 connects to operational amplifier 104 through resistor 120, diodes 122 and 124 and capacitor 126.

The switching network 14 comprises a three-to-eight line decoder 128 (a 74HC138 semiconductor chip), three AND gates 130, 132 and 134 of a quad 2 input 74HC08 semiconductor chip AND gate, four NAND 136, 138, 140 and 142 of a quad 2 input 74HC00 semiconductor chip NAND gate, a multiplexer 144 (a DG212J semiconductor chip), a 14-stage ripple carry binary counter 145 (a 4060 semiconductor chip) and a D flip-flop with preset and clear 146 of a 74HC74 semiconductor (all commercially available from National Semiconductor). Selector switch 26 with four positions 42, 44, 46 and 48 selectively connects one input of AND gates 130, 132 and 134 to ground. When not grounded, each such input is connected to a 5-volt power supply through 10K ohm resistors 150, 152 and 154 in a pre-selected manner. The output of AND gates 130, 132 and 134 connect to multiplexer 144 through NAND gates 136, 138, 140 and 142. When switch 26 is in the "auto" position 48, counter 145 actuates decoder 128 connected to AND gates 130, 132 and 134. A normally open push button switch 27 and a 10K ohm resistor 158 is connected to the CLR input of flip-flop 146, while AND gate 160 and invertor 162 are connected at the RESET input. Together these components form a starting trigger.

Comparator 16 comprises operational amplifiers 164, 166, 168 and 170 of a quad op amp TL064ACN semiconductor chip (commercially available from Texas Instruments). Operational amplifier 164 is connected to multiplexer 144 and forms a differential amplifier in conjunction with 1M ohm resistors 172 and 174, 200K ohm resistors 176 and 178 and 1-microfarad blocking capacitors 180 and 182. Operational amplifier 166 provides a 1.5 volt reference signal using the biasing provided by 10K ohm resistor 184, 40.2K ohm resistor 186, 60.4K ohm resistor 188, zener diode 190, capacitors 192 and 194. Operational amplifier 168 comprises a 60 Hz q=4 notch filter in conjunction with resistors 196, 198, 200, 202 and 204 and capacitors 206, 208 and 210 and receives the output of the differential amplifier 164. Operational amplifier 170 forms a high gain amplifier in conjunction with resistors 212, 214, and 216 and capacitor 220 and receives as one input the output of the 60 Hz notch filter.

The A/D convertor 18 comprises an ADC0804 semiconductor chip 221 and connects to comparator 16 through resistor 218. The ADC0804 semiconductor chip 221 is selectively set by the use of resistors 222, 224 and 226 and capacitors 228, 230 and 232, invertors 234 and diode 240 and drives OR gate 238 and record indicator light-emitting diode 242.

Memory means 20 connects to the A/D convertor 18 and comprises a static RAM 244 (commercially available from Hitachi Semiconductor, part No. HM62256LP-15), two 12-stage ripple carry binary counters 246 and 248 (commercially available from National Semiconductor, part No. CD4040), invertors 250, 252 and 254 of a 74HC04 hex invertor and an OR gate 256. Invertors 252 and 254 in conjunction with resistors 258 and 260 and capacitor 262 form a 450 Hz oscillator.

The D/A convertor 22 is connected to the A/D convertor 18 and the storage means 20 and includes a D/A convertor semiconductor chip 264 (commercially available from Analog Devices, Norwood, Mass.) and a filter 266. Filter 266 comprises operational amplifier 267 of a quad op amp TL064ACN, resistors 268, 270, 272 and 274 and capacitors 276 and 278. Filter 266 has a passband gain of two.

The transmission circuit 24 is connected to the D/A convertor 22 and includes VCO circuit 280, flip-flop circuit 282, operational amplifier circuit 284 and switch circuit 286. The switch assembly 286 includes a switch 28, an OR gate 288, resistors 290 and 292 and a transmit indicator light-emitting diode 294. The VCO circuit 280 connects to the D/A convertor 22 and comprises a VCO semiconductor chip 296 (commercially available from National Semiconductor, part No. LM331) and includes resistors 298, 300, 302, 304, 306, 308, 310 and 312 and capacitors 314, 316 and 318. The flip-flop circuit 282 connects to the VCO assembly 280 and comprises a 74HC74 dual flip-flop with a reset and clear 320 and includes resistors 322, 324 and 326 and capacitors 328 and 330. The operational amplifier circuit 284 connects to the flip-flop assembly 282 and comprises an operational amplifier 322 of a quad op amp TL064ACN and includes resistors 334 and 336 and capacitors 338, 340 and 342.

From the foregoing, it will be obvious to those skilled in the art that various modifications in the above-described methods can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A method of generating electrocardiographic data from a patient, said method comprising:
    placing at least three electrodes at discrete locations on the surface of said patient's body;
    selecting a first pair of said electrodes and assigning one electrode of said first pair to measure a positive polarity and the other electrode of said first pair to measure a negative polarity;
    continuously measuring the difference in electrical potential between said first pair of electrodes for a first time period of at least about 10 seconds and less than about 60 seconds;
    selecting a second pair of said electrodes different from said first pair of electrodes and assigning one electrode of said second pair to measure a positive polarity and the other electrode of said second pair to measure a negative polarity;
    continuously measuring the difference in electrical potential between said second pair of electrodes for a second time period of at least about 10 seconds and less than about 60 seconds consecutive to said first period;
    selecting a third pair of said electrodes different from said first and second pairs of electrodes and assigning one electrode of said third pair to measure a positive polarity and the other electrode of said third pair to measure a negative polarity;
    continuously measuring the difference in electrical potential between said third pair of electrodes for a third time period of at least about 10 seconds and less than about 60 seconds consecutive to said second period; and
    telemetrically transmitting or translating the chronological sequence of said measurements,
    such that said electrocardiographic data comprises the chronological sequence of said measurements of electrical potential difference.

2. The method of claim 1 wherein said time periods are of equal length.

3. The method of claim 2 wherein said time periods are each about 20 seconds long.

4. The method of claim 1 wherein said electrodes are placed on said patient's body such that said first, second and third pairs of said electrodes each correspond to a different lead in a set of ten leads in conventional electrocardiographic measurement.

5. The method of claim 4 wherein said electrodes are placed on the left arm, right arm and left leg of said patient's body.

6. The method of claim 5 wherein each of said first, second and third pairs of said electrodes corresponds to a different conventional lead selected from the group consisting of Lead I, Lead II and Lead III.

7. A method of generating electrocardiographic data from a patient, said method comprising:
    placing at least three electrodes at discrete locations on the surface of said patient's body;
    selecting a first pair of said electrodes and assigning one electrode of said first pair to measure a positive polarity and the other electrode of said first pair to measure a negative polarity;
    continuously measuring the difference in electrical potential between said first pair of electrodes for a first time period of at least about 10 seconds and less than about 60 seconds;
    continuously collecting said measurements of difference in electrical potential during said first time period for telemetric transmission or translation;
    selecting a second pair of said electrodes different from said first pair of electrodes and assigning one electrode of said second pair to measure a positive polarity and the other electrode of said second pair to measure a negative polarity;
    continuously measuring the difference in electrical potential between said second pair of electrodes for a second time period of at least about 10 seconds and less than about 60 seconds consecutive to said first period;
    continuously collecting said measurements of difference in electrical potential during said second time period for telemetric transmission or translation;
    selecting a third pair of said electrodes different from said first and second pairs of electrodes and assigning one electrode of said third pair to measure a positive polarity and the other electrode of said third pair to measure a negative polarity; and
    continuously measuring the difference in electrical potential between said third pair of electrodes for a third time period of at least about 10 seconds and less than about 60 seconds consecutive to said second period;
    continuously collecting said measurements of difference in electrical potential during said third time period for telemetric transmission or translation;
    such that said electrocardiographic data comprises the chronological sequence of said measurements of electrical potential difference.

8. The method of claim 7 wherein said measurements are collected by periodically taking digital samples from the signal corresponding to said difference in electrical potential measured along the appropriate pair of electrodes.

9. The method of claim 8 wherein said digital samples are stored for later transmission of translation.

10. The method of claim 7 further comprising:
transmitting said collected measurements to a remote site.

11. The method of claim 10 wherein said collected measurements are transmitted in digital form.

12. The method of claim 10 wherein said collected measurements are transmitted in analog form.

13. A method of generating electrocardiographic data from a patient, said method comprising:
placing a first electrode on said patient's left arm;
placing a second electrode on said patient's right arm;
placing a third electrode on said patient's left leg;
selecting said first electrode and said second electrode;
assigning said first electrode to measure a positive polarity and said second electrode to measure a negative polarity;
continuously measuring the difference in electrical potential between said first and second electrodes as an analog signal for about 20 seconds;
continuously collecting digital samples of said analog signal from said first and second electrodes;
continuously storing said digital samples for telemetric transmission;
selecting said second electrode and said third electrode;
assigning said third electrode to measure a positive polarity and said second electrode to measure a negative polarity;
continuously measuring the difference in electrical potential between said second and third electrodes as an analog signal for about 20 seconds;
continuously collecting digital samples of said analog signal from said second and third electrodes;
continuously storing said digital samples for telemetric transmission;
selecting said first electrode and said third electrode;
assigning said third electrode to measure a positive polarity and said first electrode to measure a negative polarity;
continuously measuring the difference in electrical potential between said first and third electrodes as an analog signal for about 20 seconds;
continuously collecting digital samples of said analog signal from said first and third electrodes;
continuously storing said digital samples for telemetric transmission;
reconverting said stored digital samples into analog data and transmitting said analog data;
such that said electrocardiographic data comprises said analog data.

14. A system for collecting electrocardiographic data from a patient, said system comprising:
at least three electrodes adapted for attachment to said patient from which said data is to be collected such that said electrodes form three different leads;
means for monitoring connected to said electrodes for sequentially measuring the potential difference across a first of said leads for a first time period of at least about 10 seconds and less than about 60 seconds, a second of said leads for a second time period of at least about 10 seconds and less than about 60 seconds and a third of said leads for a third time period of at least about 10 seconds and less than about 60 seconds; and
means connected to said means for monitoring for storing said sequential measurements in converted digital or analog form for telemetric transmission or translation.

15. The system of claim 14 wherein each of said leads is monitored for an equal period.

16. The system of claim 15 wherein each of said leads is monitored for about 20 seconds.

17. The system of claim 14 wherein said leads are selected from the group of conventional EKG leads consisting of Lead I, Lead II, Lead III, the aVR lead, the aVL lead, the aVF lead, the V1 lead, the V2 lead, the V3 lead, the V4 lead, the V5 lead and the V6 lead.

18. The system of claim 17 wherein said leads are selected from the group of conventional EKG leads consisting of Lead I, Lead II and Lead III.

19. The system of claim 18 wherein said first lead is Lead I, said second lead is Lead II and said third lead is Lead III.

20. The system of claim 14 wherein said sequential measurements are in analog form.

21. The system of claim 20 wherein said system further comprises means for converting said sequential measurements to digital form.

22. The system of claim 21 wherein said system further comprises means for storing said converted digital form.

23. A system for collecting electrocardiographic data from a patient, said system comprising:
at least three electrodes adapted for attachment to said patient from which said data is to be collected such that said electrodes form three different leads;
means for monitoring connected to said electrodes for sequentially measuring the potential difference across a first of said leads for a first time period of at least about 10 seconds and less than about 60 seconds, a second of said leads for a second time period of at least about 10 seconds and less than about 60 seconds and a third of said leads for a third time period of at least about 10 seconds and less than about 60 seconds; and
means connected to said means for telemetrically transmitting signals corresponding to said potential difference in converted digital or analog form to an EKG receiver to produce a signal trace serial rhythm strip.

24. A system for collecting electrocardiographic data from a patient, said system comprising:
an electrode adapted to be attached to the left arm of said patient from which said data is to be collected, an electrode adapted to be attached to the right arm of said patient and an electrode adapted to be attached to the left leg of said patient, said electrodes forming Leads I, II and III;
means connected to said electrodes for sequentially measuring analog signals representing the potential difference across Lead I, then Lead II, then Lead III for a period of 20 seconds each;
means connected to said measuring means for converting said analog signals to digital form; and
means connected to said converting means for storing said digital form of said signals for telemetric transmission or translation.

25. A system for collecting electrocardiographic data from a patient, said system comprising:

an electrode adapted to be attached to the left arm of said patient from which said data is to be collected, an electrode adapted to be attached to the right arm of said patient and an electrode adapted to be attached to the left leg of said patient, said electrodes forming Leads I, II and III;

means connected to said electrodes for sequentially measuring analog signals representing the potential difference across Lead I, then Lead II, then Lead III for a period of 20 seconds each;

means connected to said measuring means for converting said analog signals to digital form; and means connected to said converting means for transmitting said digital form of said signals to an EKG receiver to produce a single-trace serial rhythm strip.

26. A system for collecting electrocardiographic data from a patient, said system comprising:

an electrode adapted to be attached to the left arm of said patient from which said data is to be collected, an electrode adapted to be attached to the right arm of said patient and an electrode adapted to be attached to the left leg of said patient, said electrodes forming Leads I, II and III;

means connected to said electrodes for sequentially measuring analog signals representing the potential difference across Lead I, then Lead II, then Lead III for a period of 20 seconds each;

means connected to said measuring means for converting said analog signals to digital form;

means connected to said converting means for storing said digital form of said signals for telemetric transmission or translation;

means connected to said storing means for reconverting said stored signals to analog form; and means connected to said reconverting means for transmitting said signal to an EKG receiver to produce a single-trace serial rhythm strip.

27. The method of claim 7 wherein said time periods are each about 20 seconds long.

28. The method of claim 5 wherein each of said first, second and third pairs of said electrodes corresponds to a different conventional lead selected from the group consisting of aVF, aVR and aVL.

* * * * *